United States Patent [19]

Harima et al.

[11] 4,150,039
[45] Apr. 17, 1979

[54] 2,2'-BIS(3,4-EPOXY-5-OXOTETRAHY-DROPYRAN)ETHERS

[75] Inventors: Rokuro Harima; Takeshi Misawa; Tsunehiko Masatomi, all of Naruto; Yasuo Shimizu, Tokushima; Yoshifumi Nakacho, Tokushima; Hisashi Takao, Naruto; Kenji Kase, Tokushima, all of Japan

[73] Assignee: Otsuka Kagaku Yakuhin Kabushiki Kaisha, Osaka, Japan

[21] Appl. No.: 800,032

[22] Filed: May 24, 1977

[30] Foreign Application Priority Data

Jun. 15, 1976 [JP] Japan .................................. 51/70819

[51] Int. Cl.$^2$ .......................................... C07D 309/10
[52] U.S. Cl. ................................ 260/345.9 R; 424/283
[58] Field of Search ................................ 260/345.9 R

[56] References Cited

U.S. PATENT DOCUMENTS 4,059,595  11/1977  Shono et al. .................. 260/345.9 R

OTHER PUBLICATIONS

Shono et al., Tetrahedron Letters, No. 17, pp. 1363–1364 (1976).

Primary Examiner—Nicky Chan
Attorney, Agent, or Firm—Armstrong, Nikaido, Marmelstein & Kubovcik

[57] ABSTRACT 2,2'-bis(3,4-Epoxy-5-oxotetrahydropyran)ethers represented by the formula

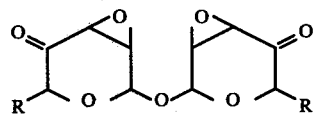

wherein R is hydrogen atom or straight-chain or branched-chain alkyl having 1 to 6 carbon atoms; a process for preparing the same.

1 Claim, No Drawings

2,2'-BIS(3,4-EPOXY-5-OXOTETRAHY-DROPYRAN)ETHERS

This invention relates to novel 2,2'-bis(3,4-epoxy-5-oxotetrahydropyran)ethers and a process for preparing the same.

The novel ethers of this invention are represented by the formula (I)

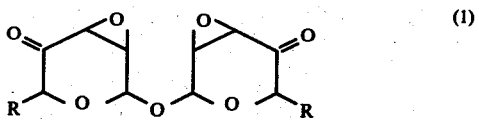

(I)

wherein R is hydrogen atom or straight-chain or branched-chain alkyl having 1 to 6 carbon atoms. Typically, the alkyl can be methyl, ethyl, propyl, isopropyl, isopropyl, n-butyl, isobutyl, pentyl, hexyl or the like.

The compounds of the formula (I) act to inhibit or prevent the growth of various bacteria, yeasts, etc. and are therefore useful as bactericidal and fungicidal agents. The compounds of this invention, when heat-treated with an acid catalyst, readily give 3-oxy-4H-pyran-4-one or 2-alkyl derivatives thereof which are serviceable as flavoring agents. Thus, the present compounds are useful also as intermediates for preparing these compounds.

Table 1 shows typical examples of the present compounds, the properties thereof, and the results obtained by subjecting them to elementary analysis and infrared absorption spectroscopy.

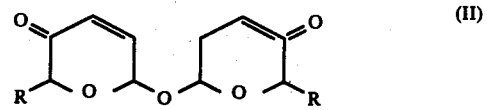

(II)

wherein R is the same as in the formula (I) with a peroxide in the presence of an alkali catalyst.

The ethers of the formula (II) useful as starting materials in this invention are known compounds to be synthesized by the process disclosed in Tetrahedron, 27, 1973-1996 (1971). The process is represented by:

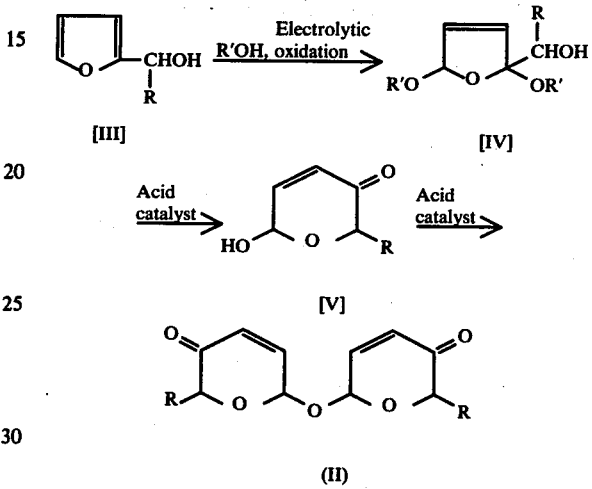

(II)

Table 1

| Comp. No. | R | Properties | Elementary analysis (%) Calcd. C , H | Found C , H | IR($\nu$ max)(cm$^{-1}$) |
|---|---|---|---|---|---|
| 1 | H | White crystals m.p. 55–58° C. | 49.5 , 4.1 | 49.6 , 4.3 | 1730 C=O stretching 1070 C—O—C stretching |
| 2 | CH$_3$ | White crystals, m.p. 114–117° C. | 53.3 , 5.1 | 53.2 , 5.1 | 1730 C=O stretching 1070 C—O—C stretching |
| 3 | CH$_2$CH$_3$ | White crystals, m.p. 131–132° C. | 56.3 , 6.0 | 56.5 , 6.0 | 1730 C=O stretching 1070 C—O—C stretching |
| 4 | n-C$_3$H$_7$ | White crystals, m.p. 142–145° C. | 58.9 , 6.7 | 58.7 , 6.5 | 1730 C=O stretching 1070 C—O—C stretching |
| 5 | iso-C$_3$H$_7$ | White crystals, | 58.9 , 6.7 | 58.7 , 6.8 | 1730 C=O stretching |
| 5 | iso-C$_3$H$_7$ | White crystals, m.p. 137–140° C. | 58.9 , 6.7 | 58.7 , 6.8 | 1730 C=O stretching 1070 C—O—C stretching |
| 6 | n-C$_4$H$_9$ | White crystals, m.p. 160–162° C. | 61.0 , 7.3 | 61.3 , 7.0 | 1730 C=O stretching 1070 C—O—C stretching |
| 7 | iso-C$_4$H$_9$ | White crystals, m.p. 146–149° C. | 61.0 , 7.3 | 61.2 , 7.4 | 1730 C=O stretching 1070 C—O—C stretching |
| 8 | n-C$_5$H$_{11}$ | White crystals, m.p. 165–167° C. | 62.8 , 7.8 | 62.9 , 7.7 | 1730 C=O stretching 1070 C—O—C stretching |
| 9 | n-C$_6$H$_{13}$ | White crystals, m.p. 174–177° C. | 64.4 , 8.3 | 64.5 , 8.2 | 1730 C=O stretching 1070 C—O—C stretching |

The compounds represented by the formula (I) can be prepared, for example, by epoxidizing the 2,2'-bis(5-oxo-5,6-dihydro-2H-pyran)ethers represented by the formula (II)

wherein R is as defined above, and R' is straight-chain or branched-chain alkyl having 1 to 4 carbon atoms.

Stated more specifically, the ethers of the formula (II) are readily prepared in high yields by electrolytically oxidizing furfuryl alcohol (III) in the presence of R'OH to obtain 2,5-dialkoxyfurfuryl alcohol (IV), treating the alcohol (IV) with an acid catalyst to enlarge the ring and dimerizing the resulting product with an acid catalyst.

Examples of useful peroxides for the epoxidizing reaction of this invention are a wide variety of known compounds such as peracetic acid, perbenzoic acid, pertirifluoroacetic acid, monochloroperbenzoic acid, monoperphthalic acid, hydrogen peroxide, tertiary butyl hydroperoxide, etc. These peroxides are usually used in an amount of about 2 to about 4 moles, preferably about 2.1 to about 3 moles, per mole of the ether starting material of the formula (II). Examples of useful alkali catalysts are hydroxides and carbonates of alkali metals, such as sodium hydroxide, potassium hydroxide, sodium carbonate, potassium carbonate, sodium hydrogencarbonate, etc. and basic ion exchange resins. Advantageously, about 0.1 to about 1 mole, preferably about 0.2 to about 0.5 mole, of such alkali catalyst is used per mole of the starting compound (II). The epoxidizing reaction of this invention proceeds favorably in a solvent. Examples of useful solvents are water; alcohols such as methanol, ethanol and isopropanol; lower aliphatic organic acids such as acetic acid and propionic acid; aliphatic ethers such as diethyl ether, diisopropyl ether, methyl cellosolve and ethyl cellosolve; cyclic ethers such as tetrahydrofuran and dioxane; esters such as ethyl acetate and butyl acetate; hydrocarbon halides such as methylene chloride, chloroform and carbon tetrachloride; etc. The expoxidizing reaction is conducted at a temperature of usually about $-30°$ to about $+40°$ C., preferably about $-20°$ to about $+20°$ C.

The compounds of this invention represented by the formula (I) are prepared by the epoxidizing reaction described above. This reaction uses as the starting material a dimerized compound (II), i.e. cyclic ether having oxygen atoms within the rings, of very complex structure wherein the oxygen atoms form part of acetal, and the epoxidizing reaction is effected with this structure retained. Thus, this reaction is entirely novel and heretofore unknown in the art.

When the system resulting from the epoxidizing reaction of this invention is free from any unreacted peroxide, the desired product can be easily isolated for recovery in usual manner, for example, by recrystallization or column chromotography. If part of the peroxide remains unreacted in the reaction mixture, it is preferable to add a solution of sodium thiosulfate to the mixture to inactivate the peroxide prior to the isolation.

The process for the preparation of the present compounds will be described below in greater detail with reference to Examples.

EXAMPLE 1

A 100 ml quantity of 5% aqueous solution of sodium carbonate is added dropwise over a period of 60 minutes to a mixture of 10.5 g of 2,2'-bis(5-oxo-5,6-dihydro-2H-pyran)-ether, 12 g of 30% aqueous solution of hydrogen peroxide and 25 cc of methanol maintained at 10° to 20° C. The resulting mixture is further reacted for 60 minutes. After the completion of the reaction, sodium thiosulfate is added to the mixture to decompose the unreacted hydrogen peroxide, the mixture is then filtered, and the filtrate is thereafter concentrated at reduced pressure. Water (50 ml) is added to the concentrate, and the mixture is extracted three times with 50-ml portions of ether. The ethereal extract is dried over magnesium sulfate. The dried extract is filtered, and the filtrate is concentrated at reduced pressure, giving 9.6 g of 2,2'-bis(3,4-epoxy-5-oxotetrahydropyran)ether in the form of white crystals, m.p. 55° to 58° C. Yield: 79.5%.

EXAMPLE 2

A 100 ml quantity of 5% aqueous solution of sodium carbonate is added dropwise over a period of 60 minutes to a mixture of 11.9 g of 2,2'-bis(6-methyl-5-oxo-5,6-dihydro-2H-pyran)ether, 12 g of 30% aqueous solution of hydrogen peroxide and 25 cc of dioxane maintained at 0° to 5° C. The resulting mixture is further reacted for 60 minutes. After the completion of the reaction, the mixture is treated in the same manner as in Example 1, giving 11.5 g of 2,2'-bis(6-methyl-3,4-epoxy-5-oxotetrahydropyran)ether in the form of white crystals, m.p. 114° to 117° C. Yield: 84.5%.

EXAMPLE 3

A 100 ml quantity of 5% aqueous solution of sodium hydrogencarbonate is added dropwise over a period of 120 minutes to a mixture of 13.3 g of 2,2'-bis(6-ethyl-5-oxo-5,6-dihydro-2H-pyran)ether, 12 g of 30% aqueous solution of hydrogen peroxide and 25 cc of acetonitrile maintained at a temperature of up to 10° C. The resulting mixture is further reacted for 60 minutes. After the completion of the reaction, the mixture is treated in the same manner as in Example 1, giving 12.8 g of 2,2'-bis(6-ethyl-3,4-epoxy-5-oxotetrahydropyran)ether in the form of white crystals, m.p. 131° to 132° C. Yield: 86.3%.

EXAMPLE 4

A b 100 ml quantity of 5% aqueous solution of sodium hydrogencarbonate is added dropwise over a period of 120 minutes to a mixture of 14.7 g of 2,2'-bis(6-isopropyl-5-oxo-5,6-dihydro-2H-pyran)ether, 12 g of 30% aqueous solution of hydrogen peroxide and 25 cc of tetrahydrofuran maintained at a temperature of up to 10° C. The resulting mixture is further reacted for 60 minutes. After the completion of the reaction, the mixture is treated in the same manner as in Example 1, giving 13.1 g of 2,2'-bis(6-isopropyl-3,4-epoxy-5-oxotetrahydropyran)ether in the form of white crystals, m.p. 137° to 140° C. Yield: 80.5%.

EXAMPLE 5

A 100 ml quantity of 5% aqueous solution of sodium hydrogencarbonate is added dropwise over a period of 60 minutes to a mixture of 15.4 g of 2,2'-bis(6-n-butyl-5-oxo-5,6-dihydro-2H-pyran)ether, 12 g of 30% aqueous solution of hydrogen peroxide and 25 cc of acetonitrile maintained at a temperature of up to 10° C. The resulting mixture is further reacted for 60 minutes. After the completion of the reaction, the mixture is treated in the same manner as in Example 1, giving 13.5 g of 2,2'-bis(6-n-butyl-3,4-epoxy-5-oxotetrahydropyran)ether in the form of white crystals, m.p. 160° to 162° C. Yield: 79.5%.

What we claimed is:

1. 2,2'-bis(3,4-Epoxy-5-oxotetrahydropyran)ethers represented by the formula

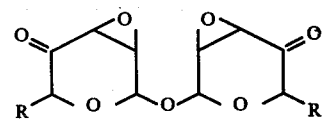

wherein R is hydrogen atom or straight-chain or branched-chain alkyl having 1 to 6 carbon atoms.

* * * * *